(12) United States Patent
Amos et al.

(10) Patent No.: US 9,841,402 B2
(45) Date of Patent: Dec. 12, 2017

(54) MULTIFUNCTION ELECTRODE WITH COMBINED HEATING AND EWOD DRIVE FUNCTIONALITY

(71) Applicant: Sharp Life Science (EU) Limited, Oxford (GB)

(72) Inventors: Robert Julian Amos, Oxford (GB); Benjamin James Hadwen, Oxford (GB); Adrian Marc Simon Jacobs, Reading (GB); Emma Jayne Walton, Oxford (GB); Christopher James Brown, Oxford (GB); Jonathan Buse, Abingdon (GB)

(73) Assignee: Sharp Life Science (EU) Limited, Oxford (GB)

( * ) Notice: Subject to any disclaimer, the term of this patent is extended or adjusted under 35 U.S.C. 154(b) by 295 days.

(21) Appl. No.: 14/686,833

(22) Filed: Apr. 15, 2015

(65) Prior Publication Data

US 2016/0305906 A1 Oct. 20, 2016

(51) Int. Cl.
*G01N 27/447* (2006.01)
*B01L 3/00* (2006.01)
*B01L 7/00* (2006.01)

(52) U.S. Cl.
CPC .. *G01N 27/44791* (2013.01); *B01L 3/502792* (2013.01); *B01L 7/52* (2013.01);
(Continued)

(58) Field of Classification Search
CPC ...... B01L 3/502792; B01L 3/502; B01L 7/52; B01L 2400/0427; B01L 2200/147; G01N 13/00; G02B 26/005
See application file for complete search history.

(56) References Cited

U.S. PATENT DOCUMENTS 6,565,727 B1 5/2003 Shenderov
6,911,132 B2 6/2005 Pamula et al.
(Continued)

FOREIGN PATENT DOCUMENTS

EP 2404675 1/2012
JP 2012-230105 11/2012
(Continued)

OTHER PUBLICATIONS

R.B. Fair, Microfluid Nanofluid, Mar. 8, 2007, 3:245-281.

*Primary Examiner* — Gurpreet Kaur
(74) *Attorney, Agent, or Firm* — Renner, Otto, Boisselle & Sklar, LLP

(57) ABSTRACT

An EWOD (or AM-EWOD) device includes a reference electrode and a plurality of array elements, each array element including an array element electrode, and control electronics. In a first mode optimized for EWOD actuation, the control electronics is configured to control a supply of time varying voltages to the array element electrodes and the reference electrode, thereby generating an actuation voltage as a potential difference between voltages at the array element electrodes and the reference electrode. The reference electrode includes a first electrical connection and a second electrical connection. In a second mode, the control electronics further is configured to supply an electrical current flow between the first electrical connection and the second electrical connection to generate resistance heat for controlling temperature of the EWOD device. Control may include sensing a temperature of the EWOD device, and switching between operating in the first or second mode based on the sensed temperature.

15 Claims, 15 Drawing Sheets

(52) U.S. Cl.
CPC .. *G01N 27/44704* (2013.01); *B01L 2200/147* (2013.01); *B01L 2300/024* (2013.01); *B01L 2300/0809* (2013.01); *B01L 2300/1827* (2013.01)

(56) References Cited

U.S. PATENT DOCUMENTS

| | | |
|---|---|---|
| 7,163,612 B2 | 1/2007 | Sterling et al. |
| 7,815,871 B2 | 10/2010 | Pamula et al. |
| 8,173,000 B1 | 5/2012 | Hadwen et al. |
| 8,339,711 B2 | 12/2012 | Hadwen et al. |
| 8,459,295 B2 | 6/2013 | Kim et al. |
| 9,248,450 B2 * | 2/2016 | Bauer ................. B01F 13/0071 |
| 2004/0055891 A1 | 3/2004 | Pamula et al. |
| 2004/0058450 A1 | 3/2004 | Pamula et al. |
| 2006/0194331 A1 | 8/2006 | Pamula et al. |
| 2011/0136109 A1 * | 6/2011 | Drechsler ............. B01L 3/5085 435/6.1 |
| 2011/0220504 A1 | 9/2011 | Casasanta, III |
| 2012/0268804 A1 * | 10/2012 | Hadwen ............ B01L 3/502792 359/290 |
| 2013/0026040 A1 | 1/2013 | Cheng et al. |

FOREIGN PATENT DOCUMENTS

| | | |
|---|---|---|
| JP | 2013-529287 | 7/2013 |
| JP | 2014-170005 | 9/2013 |

\* cited by examiner

Figure 1: PRIOR ART

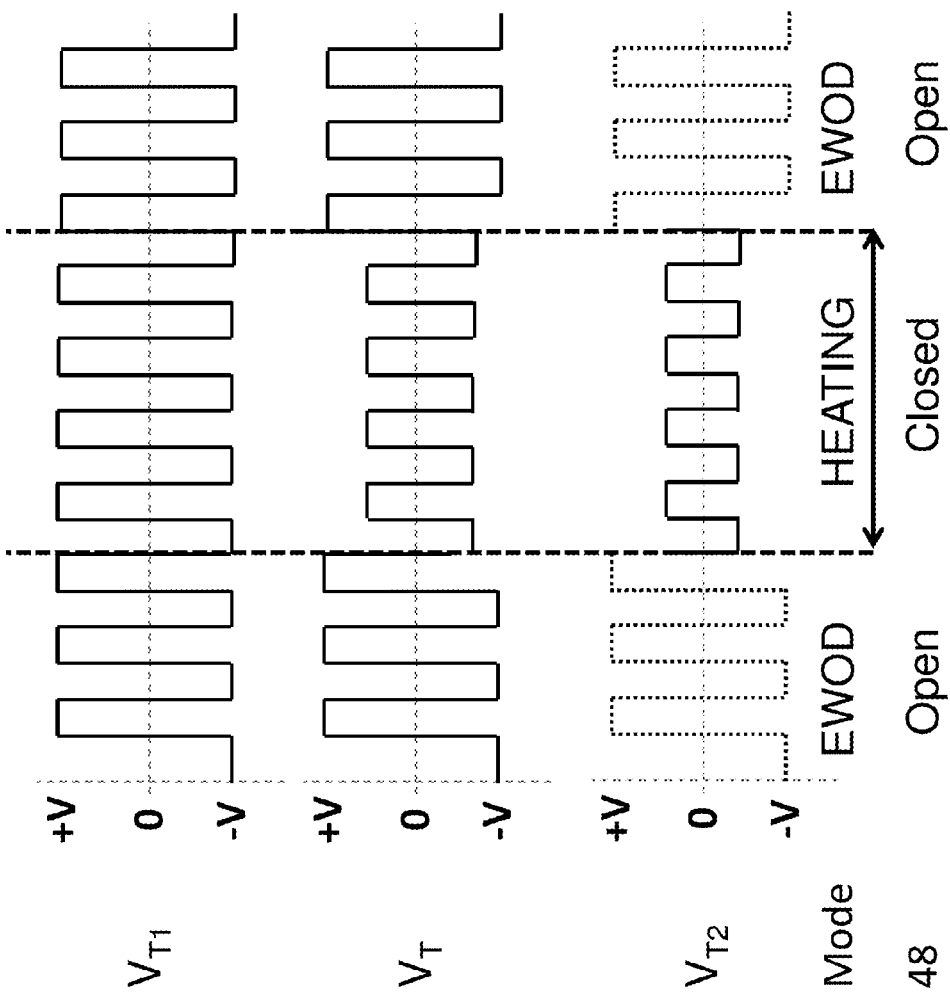

MULTIFUNCTION ELECTRODE WITH COMBINED HEATING AND EWOD DRIVE FUNCTIONALITY

TECHNICAL FIELD

The present invention relates to microfluidic devices using the Electro-wetting-On-Dielectric (EWOD) principle. EWOD is a known technique for manipulating droplets of fluid on a hydrophobic surface by means of an array of electrodes. The invention further relates to methods of simultaneously driving such a device and providing control of the temperature of the device and its contents by release of heat.

BACKGROUND ART

Electro-wetting on dielectric (EWOD) is a well-known technique for manipulating droplets of fluid by application of an electric field. It is thus a candidate technology for digital microfluidics for lab-on-a-chip technology. An introduction to the basic principles of the technology can be found in "Digital microfluidics: is a true lab-on-a-chip possible?", R. B. Fair, Microfluid Nanofluid (2007) 3:245-281).

FIG. 1 shows a part of a conventional EWOD device in cross section. The device includes a lower substrate 72, the uppermost layer of which is formed from a conductive material which is patterned so that a plurality of electrodes 38 (e.g., 38A and 38B in FIG. 1) are realized. The electrode of a given array element may be termed the element electrode 38. A liquid droplet 4, may constitute any polar (or partially polar) material (which is commonly also aqueous and/or ionic), and is constrained in a plane between the lower substrate 72 and a top substrate 36. A suitable gap between the two substrates may be realized by means of a spacer 32, and a non-polar fluid 34 (for example an oil, for example dodecane or silicone oil or any other alkane or mineral oil) may be used to occupy the volume not occupied by the liquid droplet 4. Alternatively, and optionally, the volume not occupied by the liquid droplet could be filled with air. An insulator layer 20 disposed upon the lower substrate 72 separates the conductive electrodes 38A, 38B from a first hydrophobic surface 16 upon which the liquid droplet 4 sits with a contact angle 6 represented by θ. On the top substrate 36 is a second hydrophobic layer 26 with which the liquid droplet 4 may come into contact. Interposed between the top substrate 36 and the second hydrophobic layer 26 is a top substrate electrode 28.

The contact angle θ 6 is defined as shown in FIG. 1, and is determined by the balancing of the surface tension components between the solid-liquid ($\gamma_{SL}$), liquid-gas ($\gamma_{LG}$) and non-polar fluid ($\gamma_{SG}$) interfaces, and in the case where no voltages are applied satisfies Young's law, the equation being given by:

$$\cos\theta = \frac{\gamma_{SG} - \gamma_{SL}}{\gamma_{LG}} \qquad \text{(equation 1)}$$

In certain cases, the relative surface tensions of the materials involved (i.e. the values of $\gamma_{SL}$, $\gamma_{LG}$ and $\gamma_{SG}$) may be such that the right hand side of equation (1) is less than −1. This may commonly occur in the case in which the non-polar fluid 34 is oil. Under these conditions, the liquid droplet 4 may lose contact with the hydrophobic surfaces 16 and 26, and a thin layer of the non-polar fluid 34 (oil) may be formed between the liquid droplet 4 and the hydrophobic surfaces 16 and 26.

In operation, voltages termed the EW drive voltages, (e.g. $V_T$, $V_O$ and $V_{OO}$ in FIG. 1) may be externally applied to different electrodes (e.g. element electrodes 38, 38A and 38B, respectively). The resulting electrical forces that are set up effectively control the hydrophobicity of the hydrophobic surface 16. By arranging for different EW drive voltages (e.g. $V_O$ and $V_{OO}$) to be applied to different element electrodes (e.g. 38A and 38B), the liquid droplet 4 may be moved in the lateral plane between the two substrates 72 and 36.

U.S. Pat. No. 6,565,727 (Shenderov, issued May 20, 2003) discloses a passive matrix EWOD device for moving droplets through an array.

U.S. Pat. No. 6,911,132 (Pamula et al., issued Jun. 28, 2005) discloses a two dimensional EWOD array to control the position and movement of droplets in two dimensions.

U.S. Pat. No. 6,565,727 further discloses methods for other droplet operations including the splitting and merging of droplets, and the mixing together of droplets of different materials.

U.S. Pat. No. 7,163,612 (Sterling et al., issued Jan. 16, 2007) describes how TFT based electronics may be used to control the addressing of voltage pulses to an EWOD array by using circuit arrangements very similar to those employed in active matrix (AM) display technologies.

The approach of U.S. Pat. No. 7,163,612 may be termed "Active Matrix Electro-wetting on Dielectric" (AM-EWOD). There are several advantages in using TFT based electronics to control an EWOD array, namely:

Driver circuits can be integrated onto the AM-EWOD array substrate.

TFT-based electronics are well suited to the AM-EWOD application. They are cheap to produce so that relatively large substrate areas can be produced at relatively low cost.

TFTs fabricated in standard processes can be designed to operate at much higher voltages than transistors fabricated in standard CMOS processes. This is significant since many EWOD technologies require EWOD actuation voltages in excess of 20V to be applied.

A disadvantage of U.S. Pat. No. 7,163,612 is that it does not disclose any circuit embodiments for realizing the TFT backplane of the AM-EWOD.

EP2404675 (Hadwen et al., published Jan. 11, 2012) describes array element circuits for an AM-EWOD device. Various methods are known for programming the array and applying an EWOD actuation voltage to the EWOD element electrode. The voltage write function described includes a memory element of standard means, for example, based on Dynamic RAM (DRAM) or Static RAM (SRAM), and input lines for programming the array element. Whilst EWOD (and AM-EWOD) devices can be operated with either DC or AC actuation voltages, in practice there are many reasons for preferring an AC method of driving, as reviewed in the previously cited reference R. B. Fair, Microfluid Nanofluid (2007) (3:245-281). It may be noted that droplets can be actuated and manipulated for a wide range of AC driving frequencies ranging typically from a few hertz to several kHz.

A method for implementing an AC driving method in an AM-EWOD device is to apply a ground potential to the top substrate electrode 28. To program a given element electrode in the array to a non-actuated state, the element electrode is written to a ground potential. To program a given array element electrode 38 to an actuated state, the element electrode potential 38 is written to have a potential that alternates between $V_{EW}$ and $-V_{EW}$. However this method of driving has the significant disadvantage that the maximum voltage that must be switched by the transistors in the circuit in order to drive the element electrode 38 is required to be $2V_{EW}$.

U.S. Pat. No. 8,173,000 (Hadwen et al., issued May 8, 2012) describes an AM-EWOD device with array element circuit and method for writing an AC actuation voltage to the electrode. The AC drive scheme described by this patent utilizes the application of AC signals to both the element electrode 38 and to the top substrate electrode 28 of the device. Therefore, the device is capable of generating an electro-wetting voltage (voltage between the element electrode and the top substrate electrode 28) that varies between $+V_{EW}$ and $-V_{EW}$, whilst the transistors in the array element circuit are only ever required to operate with a rail-to-rail voltage of $V_{EW}$.

Many applications of EWOD technology require that the temperature of liquid droplets be controlled and/or varied. Examples include molecular diagnostics, material synthesis and nucleic acid amplification. A number of approaches have been taken to providing temperature control in a microfluidic device. One approach to achieving thermal control is to control the temperature of the entire device and its housing by external means, e.g. a hot plate. This suffers from the disadvantages that the rates of temperature change that can be achieved are generally low, and that a long time is required for the whole arrangement to reach thermal equilibrium. A number of other approaches to address this problem have been described.

U.S. Pat. No. 7,815,871 (Pamula et al, issued Oct. 19, 2010) discloses a droplet microactuator system incorporating an EWOD device with one or more heating zones for temperature control.

U.S. Pat. No. 8,459,295 (Kim et al, issued 11 Jun. 2013) discloses a microfluidic device for droplet manipulation according to the EWOD principle, wherein one or more of the electrodes on the bottom substrate comprises a heating element in the form of a patterned electrode.

U.S. Pat. No. 8,339,711 (Hadwen et al, issued Dec. 25, 2012) discloses an AM-EWOD device, with heater elements realized in the same conductive layer that is used to control droplet motion.

US20130026040 (Cheng et al, application published Jan. 31, 2013) discloses a microfluidic platform comprising an AM-EWOD device with an active matrix array of independently addressable heating elements, which may be formed in the same or different substrates, above or below a droplet handling area. This arrangement provides for independent actuation and heating of liquid droplets.

Each of these approaches has disadvantages, with many of them involving multiple layers of patterned material that must be aligned with one another, adding complexity and cost to the manufacturing process. This is an important consideration for Lab on a Chip applications, particularly where the chip must be disposable for reasons such as biological or chemical contamination of the surfaces by the reagents and samples that are used.

SUMMARY OF INVENTION

An EWOD device is provided having a reference electrode to which at least two separate electrical connections are made, connection A and connection B. The device may operate in two modes: an EWOD mode to achieve actuation of droplets by electrowetting, and a heating mode to control the temperature of the droplets in the device. The EWOD mode may be achieved by supplying one or both of connections A and B with a voltage signal, whilst the electrodes of the lower substrate are also driven with suitable voltage signals. The heating mode may be achieved by supplying connections A and B with a voltage signal such that the voltage signals supplied to connection A and connection B are different. Heat is therefore dissipated in the reference electrode by Joule heating. The resistance of the reference electrode and /or the voltage signals supplied to connections A and B may be chosen such that simultaneous droplet actuation and Joule heating may occur.

An aspect of the invention, therefore, is an electrowetting on dielectric (EWOD) device. In exemplary embodiments, the EWOD device includes a reference electrode, a plurality of array elements, each array element including an array element electrode, and control electronics. The control electronics is configured to control a supply of time varying voltages to the array element electrodes and the reference electrode, thereby generating an actuation voltage as a potential difference between voltages at the array element electrodes and the reference electrode. The reference electrode includes a first electrical connection and a second electrical connection, and the control electronics further is configured to supply an electrical current flow between the first electrical connection and the second electrical connection to generate resistance heat for controlling temperature of the EWOD device. The EWOD device may be an active matrix electrowetting on dielectric (AM-EWOD) device.

The control electronics further may include a switch that is switchable between an open position and a closed position. The open position corresponds to an EWOD actuation mode in which there is no current flow between the first electrical connection and the second electrical connection to optimize EWOD actuation, and the closed position corresponds to a heating mode in which current flows between the first electrical connection and the second electrical connection to generate the resistance heat for controlling temperature of the EWOD device.

Another aspect of the invention is a method of controlling the EWOD (or AM-EWOD) device. In exemplary embodiments, the control method includes the steps of: operating in a first mode for optimized EWOD actuation by supplying time varying voltages to the array element electrodes and the reference electrode, thereby generating an actuation voltage as a potential difference between voltages at the array element electrodes and the reference electrode; and operating in a second mode for temperature control further by supplying an electrical current flow across the reference electrode to generate resistance heat for controlling temperature of the EWOD device. The control method further may include sensing a temperature of the EWOD device, and switching between operating in the first mode or the second mode based on the sensed temperature.

In described embodiments of the invention, the EWOD device is implemented as an AM-EWOD, although the invention is not intended to be limited to active matrix type EWOD devices in the broadest sense.

The advantages of the device are:
The heater is in close proximity to the droplet on the array, which allows for more efficient and finer control of its temperature, and for more rapid changes.
The capability of the top substrate to perform a heating function simultaneously with EWOD actuation means that one or more droplets can be manipulated to perform functions such as holding them place, and actively mixing or moving them on the array without interruption to the heating, as is required by some systems incorporating multifunction electrodes.

The use of a single conductive layer for both EWOD and heating purposes preserves the simplicity of the design and manufacture of EWOD devices.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF DRAWINGS

In the annexed drawings, like references indicate like parts or features:

FIG. 7 depicts their change over time and in EWOD actuation and heating modes, according to an exemplary method of driving the reference electrode using the circuit of FIG. 6;

FIG. 13 depicts their change over time and in EWOD actuation and heating modes, according to an exemplary method of driving the reference electrode using the circuit of FIG. 12;

FIG. 15 is a graphical representation of the voltages $V_{T1}$ and $V_{T2}$ that are connected to the reference electrode of FIG. 5 and the voltage observed on the electrode itself. FIG. 15 depicts their change over time and in EWOD actuation and heating modes, according to an exemplary method of driving the reference electrode using the circuit of FIG. 14.

DESCRIPTION OF REFERENCE NUMERALS

Figure 1:
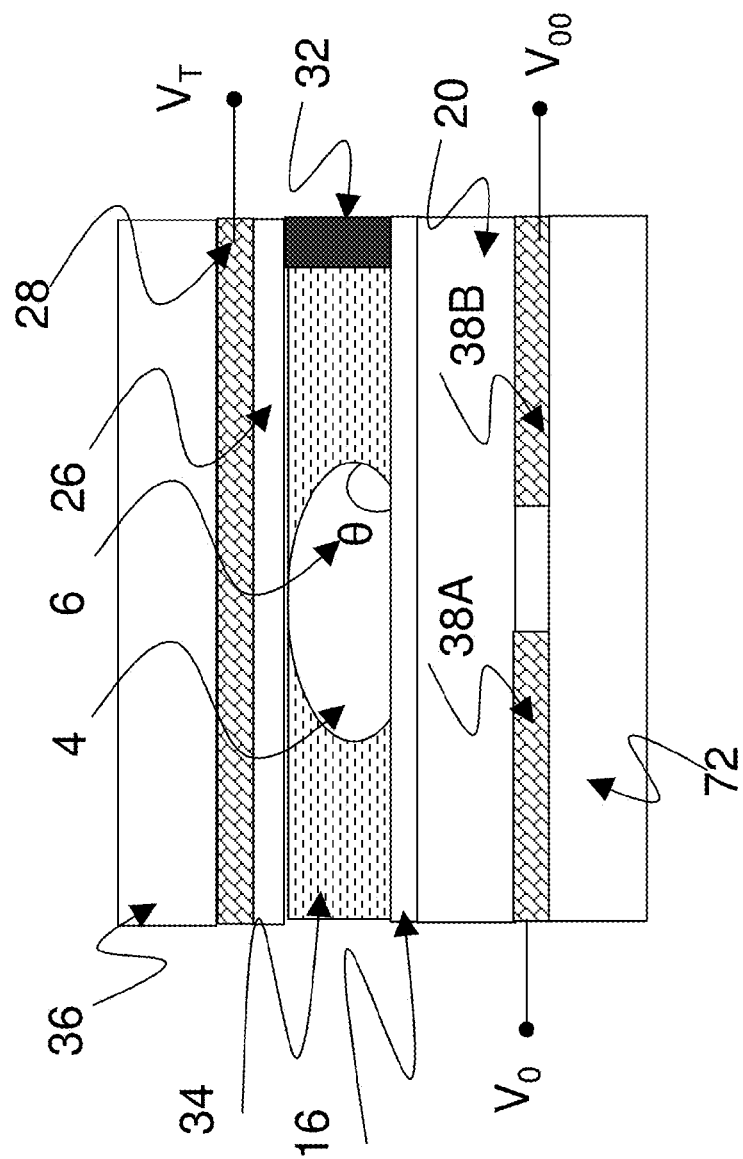
FIG. 1 shows prior art and is a schematic diagram depicting a conventional EWOD device in cross-section.

A, B connections to the reference electrode
4 liquid droplet
6 contact angle θ
16 First hydrophobic surface
20 Insulator layer
26 Second hydrophobic surface
28 Reference electrode
31 In-plane counter electrode
32 Spacer
34 Non-polar fluid
36 Top substrate
38/38A and 38B Array Element Electrodes
40 Reader
41 AM-EWOD device
42 Electrode array
43 Control electronics
45 Non-Transitory computer readable medium
44 Cartridge
46/46A and 46B Powered output amplifier
48 Single-pole, single-throw switch
50 Resistor
52 Low resistance zone
54 High resistance zone
56 Double pole double throw four-way switch
72 Substrate
74 Thin film electronics
82 Connecting wires
84 AC voltage supply
86 DC voltage supply

DETAILED DESCRIPTION OF INVENTION

Figure 2:
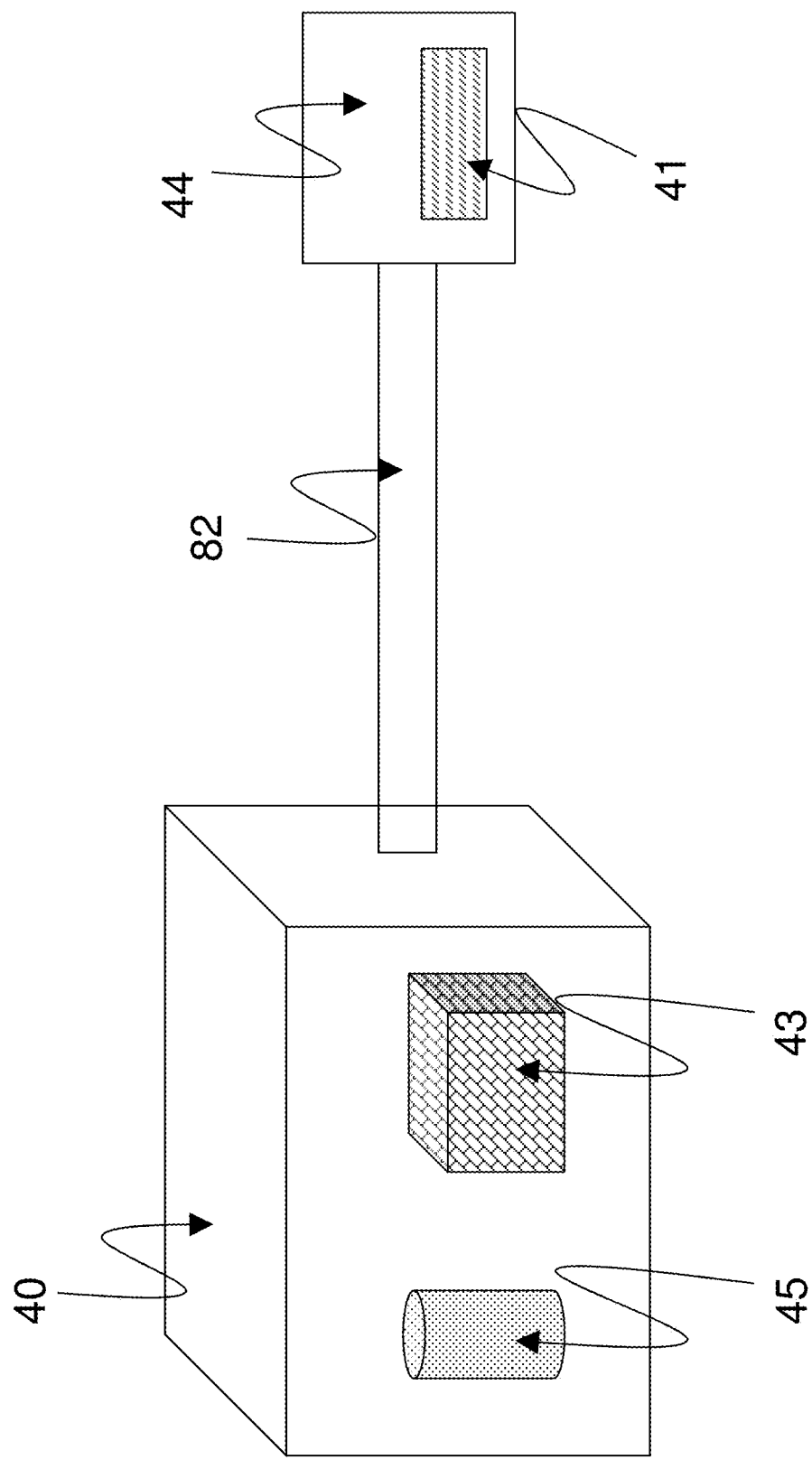
FIG. 2 shows an exemplary assay measurement system according to a first embodiment of the invention.

FIG. 2 shows an exemplary droplet microfluidic handling system according to an exemplary first embodiment of the present invention. The system is in two parts including a reader 40 and a cartridge 44.

The cartridge 44 may contain an AM-EWOD device 41 as well as (not shown) fluid input ports into the device, and an electrical connection. The fluid input ports may perform the function of inputting fluid into the AM-EWOD device 41 and generating droplets 4 within the device, for example by dispensing from input reservoirs as controlled by electrowetting. Optionally, the cartridge 44 may also contain external heaters and coolers (not shown), which may perform the function of controlling the internal temperature of the cartridge, for example by Joule heating or the Peltier effect. As referenced above, in described embodiments of the invention, the EWOD device is implemented as an AM-EWOD, although the invention is not intended to be limited to active matrix type EWOD devices in the broadest sense.

The reader 40 may contain control electronics 43 and a non-transitory computer readable medium 45 storing application software. The application software may be a computer program containing computer code which when executed by a computer is configured to perform some or all of the following functions:

- Define the appropriate timing signals to manipulate liquid droplets 4 on the AM-EWOD device 41.
- Interpret input data representative of sensor information measured by the AM-EWOD device 41, including computing the locations, sizes, centroids and perimeters of liquid droplets on the AM-EWOD device 41.
- Use calculated sensor data to define the appropriate timing signals to manipulate liquid droplets on the AM-EWOD device 41, i.e. acting in a feedback mode.
- Define appropriate signals to the control the temperature of the AM-EWOD device 41 by modulation of one or more heaters or coolers (not shown), including those integrated within the AM-EWOD device 41.
- A graphical user interface (GUI) whereby the user may program commands such as droplet operations (e.g. move a droplet), assay operations (e.g. perform an assay), and which may report the results of such operations to the user.

The control electronics 43 may supply the required voltage and timing signals to the cartridge 44 in order to manipulate and sense liquid droplets 4 on the AM-EWOD device 41. The control electronics 43 may also supply the required voltage and timing signals for heating circuits in order to control the temperature of the droplets 4 in AM-EWOD device 41.

The reader 40 and cartridge 44 may be connected together whilst in use, for example by a cable of connecting wires 82, although various other methods of making electrical communication may be used as is well known.

Figure 3:
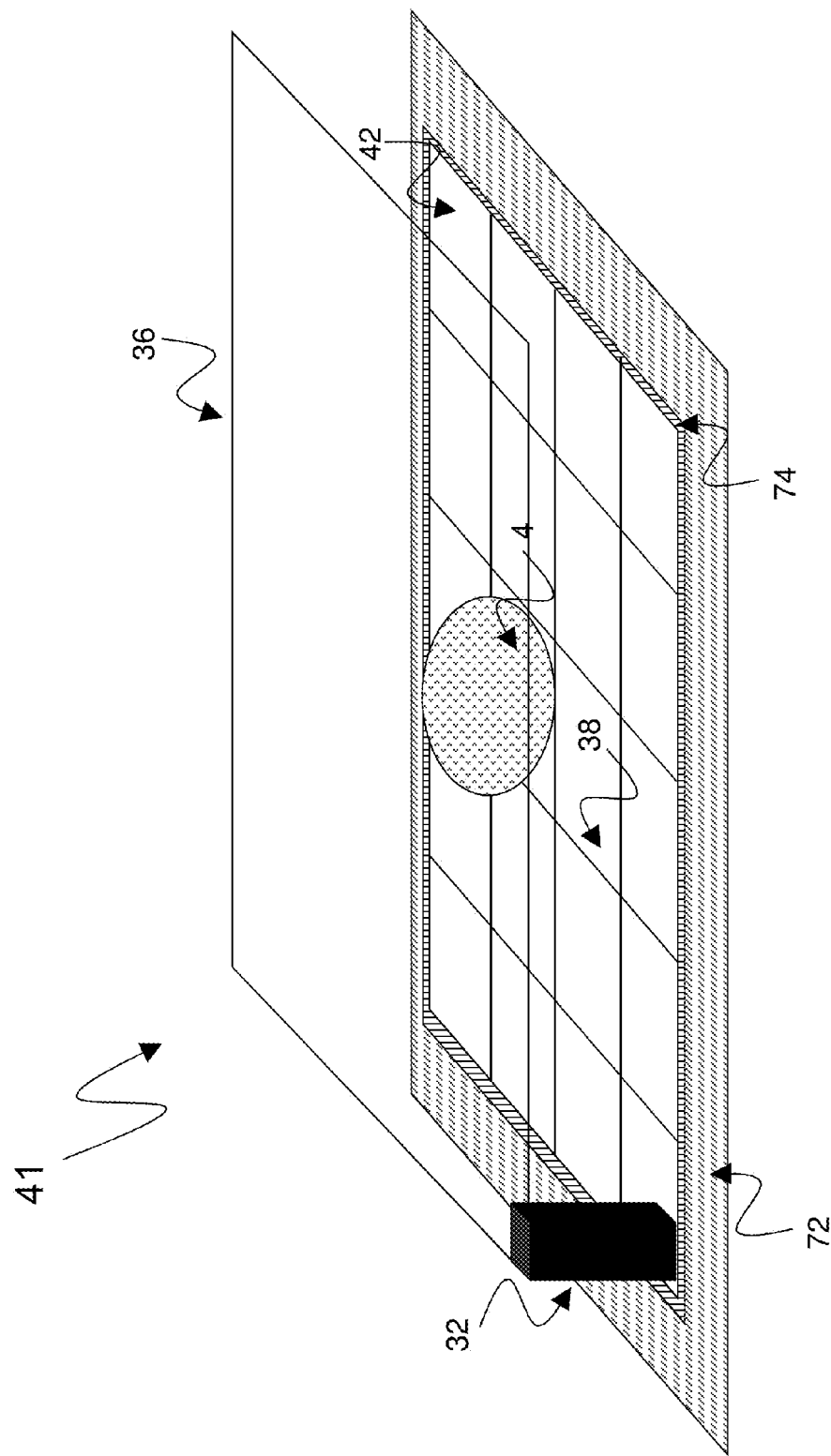
FIG. 3 shows a schematic of the EWOD device according to an exemplary first embodiment of the invention.

FIG. 3 is a schematic diagram depicting an AM-EWOD device 41 that may form part of the cartridge 44 in accordance with an exemplary embodiment of the invention. The AM-EWOD device 41 has a lower substrate 72 with thin film electronics 74 disposed upon the lower substrate 72. The thin film electronics 74 includes at least a portion of the control electronics, and are arranged to drive the array element electrodes 38. A plurality of array element electrodes 38 are arranged in an electrode array 42, having X by Y elements where X and Y may be any integer. A liquid droplet 4 which may constitute any polar liquid and which typically may be aqueous, is enclosed between the lower substrate 72 and a top substrate 36, although it will be appreciated that multiple liquid droplets 4 can be present.

Figure 4:
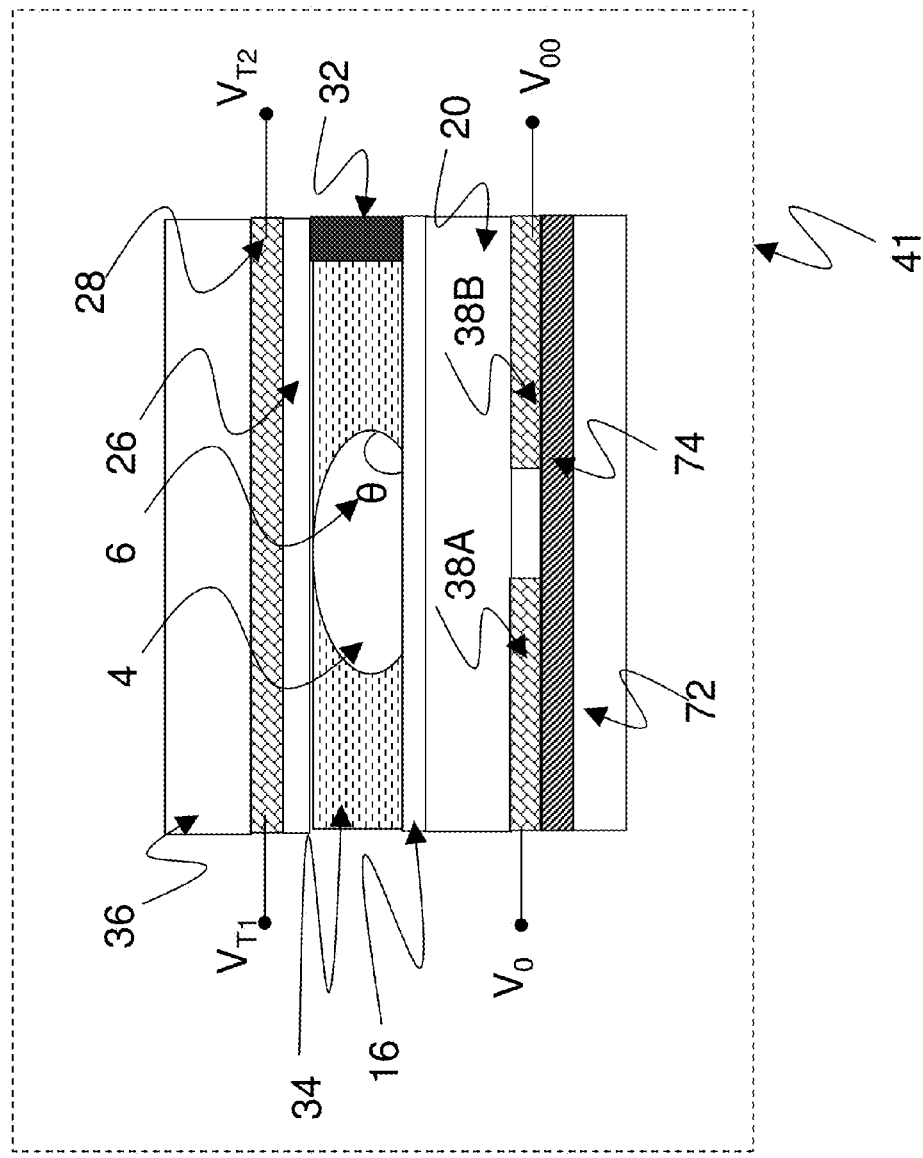
FIG. 4 shows a cross section through some of the array elements of the exemplary AM-EWOD device of FIG. 3, and illustrating the principle by which a potential difference is created to produce joule heating in the reference electrode, in accordance with a first and exemplary embodiment of the invention.

FIG. 4 is a schematic diagram depicting an AM-EWOD device 41, such as the device of FIG. 3, in cross-section and including a pair of the array elements including a plurality of array element electrodes 38A and 38B. The device configurations of FIGS. 3 and 4 bear similarities to the conventional configuration shown in FIG. 1, with the AM-EWOD device 41 of FIGS. 3 and 4 further incorporating the thin-film electronics 74 disposed on the lower substrate 72. The uppermost layer of the lower substrate 72 (which may be considered a part of the thin film electronics layer 74) is patterned so that a plurality of the array element electrodes 38 (e.g., 38A and 38B in FIG. 4) are realized. The array element electrodes 38 collectively may be termed the electrode array 42. The term array element electrode may be taken in what follows to refer both to the electrode 38 associated with a particular array element, and also to the node of an electrical circuit directly connected to this electrode 38.

The term reference electrode 28 may be understood in all that follows to mean the most general structure for providing a reference potential to liquid droplet 4. The term reference electrode 28 may thus be considered to describe a structure including any, or multiple, of a top substrate electrode 28, an in-plane counter electrode 31 or some other means of connecting an electrically conductive structure to the droplet, e.g. a catena. The reference electrode 28 may also be directly in contact with the liquid droplet 4, or may contact the liquid droplet 4 via an insulator layer and/or hydrophobic coating layer. The term reference electrode 28 also is used to describe the electrical circuit node corresponding to the physical reference electrode structure.

Figure 5:
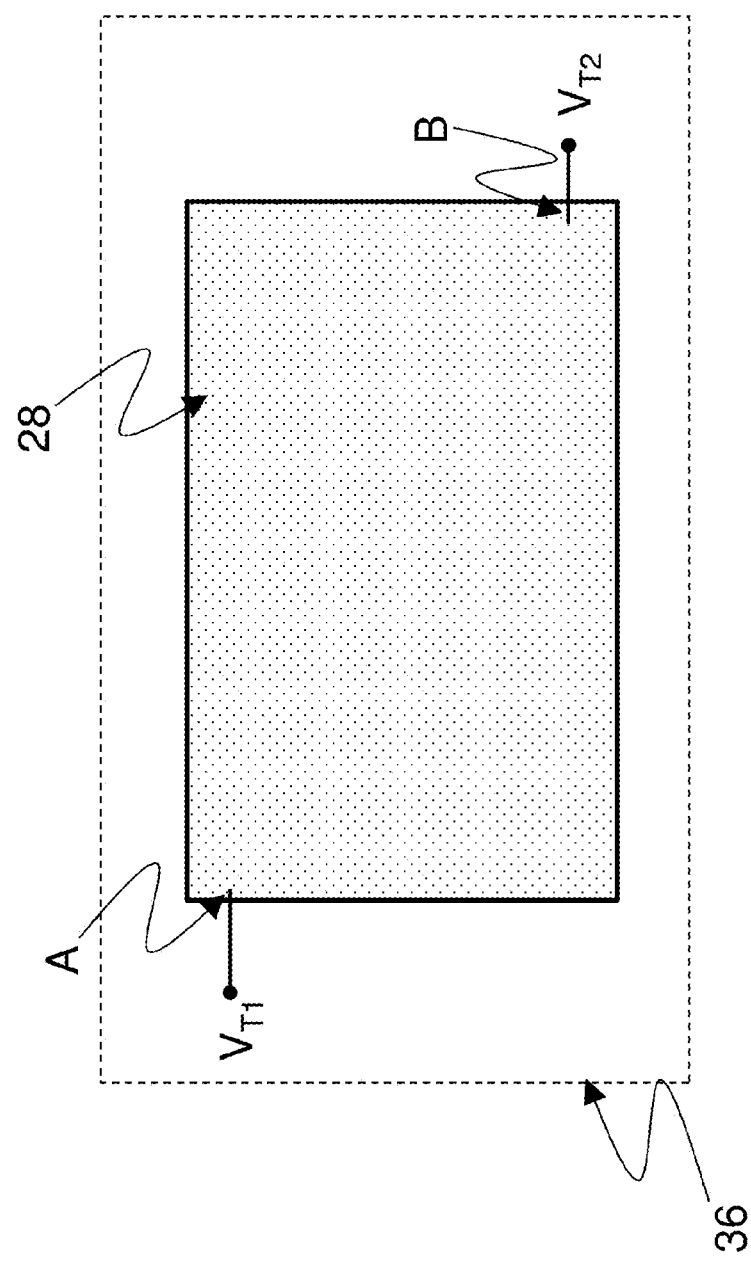
FIG. 5 is a schematic diagram depicting an overhead view of the top substrate of the exemplary AM-EWOD device of FIG. 4, and an exemplary method of making connections so as to allow EWOD actuation and heating.

FIG. 5 is a schematic diagram depicting the top substrate 36 of the AM-EWOD device 41 of FIG. 3 in an overhead view, according to a first, exemplary embodiment of the invention. The reference electrode 28 may be made of a layer of an electrically conductive material, such as metal, polysilicon, or conductive oxide materials such as indium tin oxide (ITO). The electrical sheet resistance of the conductive layer may typically be between 0.5 and 500 $\Omega$/sq. Optionally and preferably, transparent conductive materials (e.g. ITO) may be used to enable optical measurement techniques such as fluorescence in order to characterize the reactions occurring in a droplet 4 inside the AM-EWOD device 41 in real time. Optionally the reference electrode may be patterned using well known techniques such as photo-lithography, etching, or other suitable technique. to facilitate local variations in the sheet resistance of the reference electrode 28. Low resistance electrical contacts may be made by standard techniques such as soldering, and allow the reference electrode 28 to be driven with voltages at connections A and B, these voltages being termed $V_{T1}$ and $V_{T2}$ as shown in FIG. 5.

In general, the control electronics is configured to control a supply of time varying voltages to the array element electrodes and the reference electrode to operate in a first mode optimized for EWOD actuation. In this first mode, an actuation voltage is generated as a potential difference between voltages at the array element electrodes and the reference electrode. In addition, as referenced above the reference electrode includes a first electrical connection A and a second electrical connection B. The control electronics further is configured to operate in a second mode to supply an electrical current flow between the first electrical connection and the second electrical connection. In this second mode, which is referred to herein at times as a heating mode, the additional current flow through the reference electrode between connections A and B generates resistance heat for controlling temperature of the AM-EWOD device.

Figure 6:
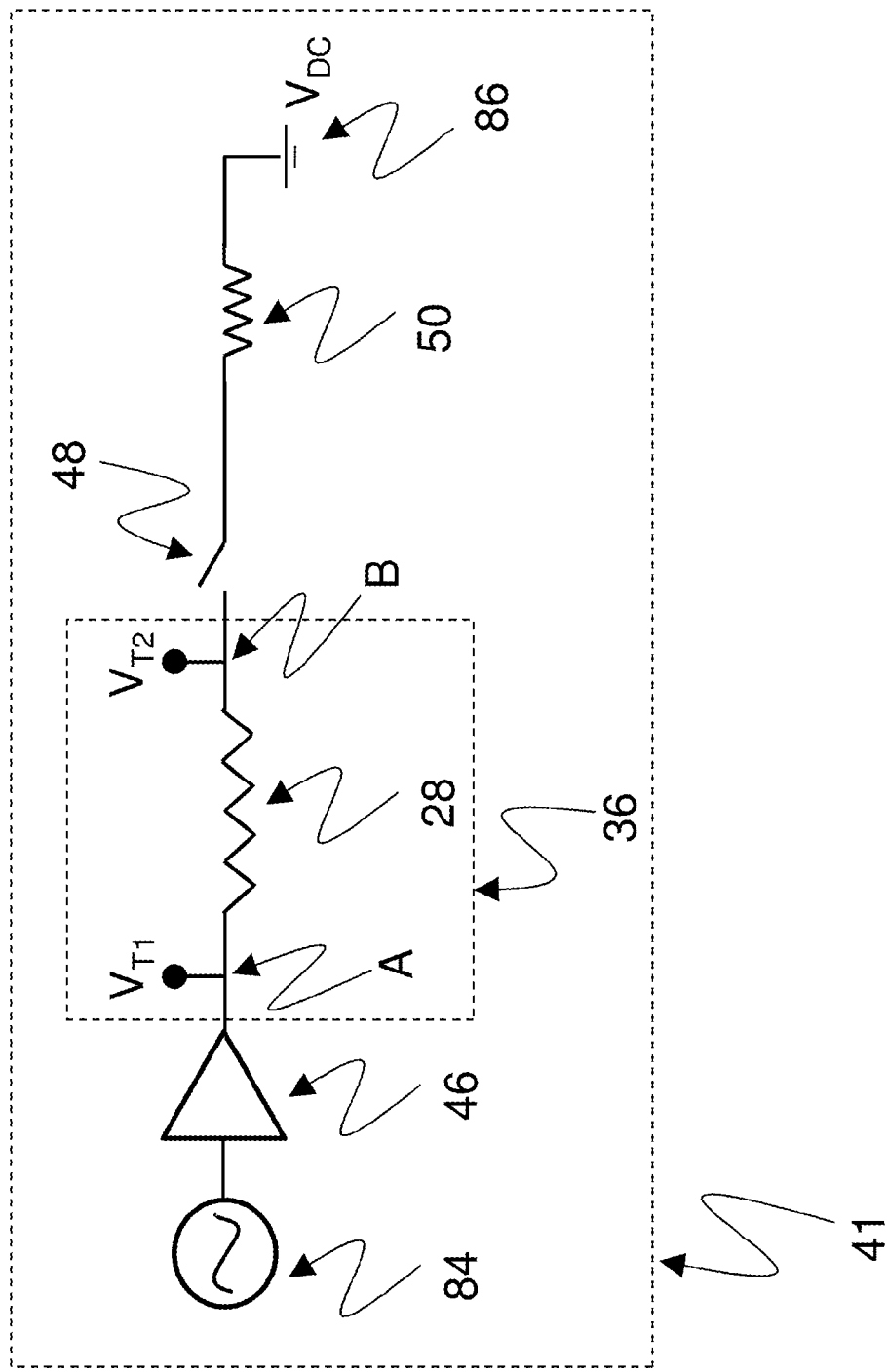
FIG. 6 shows a circuit representation of the reference electrode and its electrical connections in FIG. 5 according to a first embodiment, allowing it to be driven to achieve EWOD actuation and joule heating.

FIG. 6 shows a circuit representation of the reference electrode 28 of FIG. 5, the electrical connections A and B, and voltage supplies that are used to drive the reference electrode for EWOD actuation and heating, according to a first exemplary embodiment. Since the reference electrode 28 is a conductor, it can be considered as part of an electrical circuit. In order to facilitate efficient heating of the reference electrode 28, its resistance should form a significant proportion of the total resistance of the heating circuit. The reference electrode is modelled in FIG. 6 as a resistor, with terminal connections $V_{T1}$ and $V_{T2}$. In the circuit in FIG. 6, the terminal connection A is connected to a first voltage supply, such as an AC voltage supply 84, which supplies the voltage used as a reference voltage for EWOD actuation and for joule heating during the heating mode. Optionally, as is shown in FIG. 6, an output amplifier 46 may be incorporated between the AC voltage supply 84 and the reference electrode 28 in order to maintain the signal voltage when a current is drawn, such as when the circuit is in heating mode. The reference electrode 28 is connected via terminal B to a switch 48, which is in turn connected to a second voltage supply, such as DC voltage supply 86, via a resistor 50. The disposition of the different parts of the circuit within the AMEWOD device 41 are shown by their positions within boxes representing the top substrate 36 and the AMEWOD device 41, though some of the elements that are shown as external to the top substrate 36 could equally be incorporated into its structure.

As has been previously outlined, the circuit is designed to operate in two modes: a first, EWOD mode optimised for EWOD actuation, and a second heating mode in which current is allowed to flow through the reference electrode 28. In this embodiment the mode is selected by the switch 48 that is switchable between an open position corresponding to the first mode, and a closed position corresponding to the second mode.

In the first EWOD mode, switch 48 is open and the reference electrode is driven by the AC voltage supply 84, resulting in an AC signal $V_{T1}$ at connection A, with minimal flow of current. In the second heating mode, switch 48 is closed, making a connection to the DC voltage supply 86 and allowing current to flow through the reference electrode 28 between connection A at voltage $V_{T1}$ and connection B at voltage $V_{T2}$. In an AM-EWOD device 41 using TFT electronics for EWOD drive, typically a DC voltage between −20 and +20V may be used. Switch 48 may be operated according to a duty cycle, and by varying the proportion of the time spent in heating mode the level of heating and thereby the temperature of the AM-EWOD device 41 can be controlled. The temperature that is achieved in the AM-EWOD device 41 may be sensed and measured using standard means such as thermistors and thermocouples, and may be controlled by coupling the heat output, for example through the duty cycle of the heating mode, with a closed-loop feedback mechanism using the measured temperature as an input, such as a proportional-integral-derivative (PID) controller. The power that is required to achieve temperature will be dependent on the design and environment of the cartridge 44 in which the AM-EWOD device 41 is mounted. Accordingly, temperature control of the AM-EWOD device may be performed by sensing a temperature of the AM-EWOD device, and switching between operating in the first mode or the second mode based on the sensed temperature.

It should be noted that during the heating mode, the EWOD reference signal will continue to be present, allowing EWOD actuation of the droplet 4. Across the reference electrode 28, the EWOD reference voltage $V_T$ that is observed will however be attenuated from the level of the voltage $V_{T1}$ at connection A, sourced from the AC voltage supply 84, towards the level of the DC voltage $V_{T2}$ that is applied at connection B. The attenuation that will occur at any respective point on the reference electrode 28 will be in proportion to the resistance of the reference electrode 28 between such respective point and connection A, relative to the resistance of the whole circuit, i.e. between the AC voltage supply 84 and the DC voltage supply 86 in FIG. 6. The attenuation effect during heating mode is shown in FIG. 7.

Figure 7:
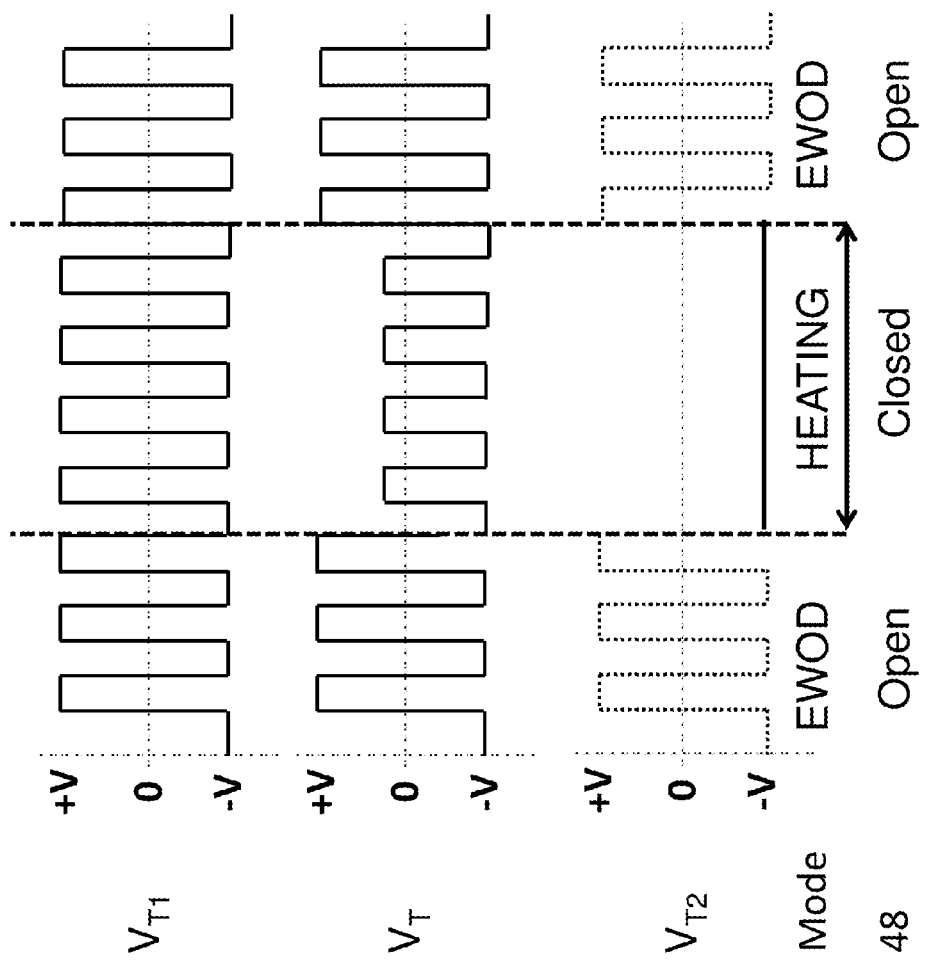
FIG. 7 is a graphical representation of the voltages $V_{T1}$ and $V_{T2}$ that are connected to the reference electrode of FIG. 5 and the voltage observed on the electrode itself.

FIG. 7 is a graphical representation of the voltages $V_{T1}$ and $V_{T2}$ observed at connections A and B as labelled in FIG. 6, and in the effective reference voltage for EWOD actuation $V_T$ at a location in the middle of the reference electrode 28 (not shown), over a short period of time. FIG. 7 displays examples of the voltages $V_{T1}$ and $V_{T2}$ observed at connections A and B and the effective reference voltage for EWOD actuation in the reference electrode 28, $V_T$. The waveform for $V_{T1}$ shows how it may be driven by the AC voltage supply 84, varying between arbitrary voltages of +V and −V. During EWOD mode, switch 48 is open and both the reference electrode 28 voltage $V_T$ and $V_{T2}$ at connection B are driven only by the AC voltage supply and thus they follow the same waveform. In the case of $V_{T2}$, the waveform during this period is shown as a dotted line to emphasise that it is passively driven. When switch 48 is closed, heating mode is entered and connection B is now connected to, and actively driven by, the DC voltage supply 86 to produce the voltage now seen as $V_{T2}$. In the heating mode, $V_T$ is driven by both the AC voltage $V_{T1}$ connected at connection A and the DC voltage $V_{T2}$ connected at connection B. In the exemplary method driving shown in FIG. 7, the DC voltage supply is set to −V, with the result that $V_{T2}$ assumes a voltage close to −V and the waveform seen at $V_T$ is therefore an attenuated version of the AC waveform superimposed on a baseline of −V. It will be apparent that other DC voltages including 0V or +V could however be used for the DC voltage supply 86.

The effect of this attenuation of the AC signal will result in a reduced potential difference between the reference EWOD voltage $V_T$ in the reference electrode 28 and the voltage $V_0$ on the array element electrodes 38 used for EWOD drive. In the case where the frequency of the AC waveform is below the characteristic droplet response frequencies (as determined by the droplet conductivity), the effective electrowetting voltage $V_{EWOD}$ is given by the root mean square (rms) value of the voltage difference between the voltage $V_T$ on the reference electrode 28, and the voltage $V_0$ on the array element 38. The electrowetting effect and the resulting actuation force that can be generated depend on $V_{EWOD}$. The attenuation of the reference EWOD voltage $V_T$ will therefore result in a reduction in the effectiveness of EWOD actuation, and in parts of the reference electrode 28 close to the connection B driven at $V_{T2}$, the attenuation may be such that $V_{EWOD}$ is no longer sufficient to perform operations that require a powerful EWOD driving force, such as splitting a droplet 4 into two. $V_{EWOD}$ may nevertheless be maintained adequately to perform a low-voltage droplet operation. For example, the low-voltage droplet operation may be to allow the position of a droplet 4 on the electrode array 42 to be maintained during the heating period, since this does not require as strong an EWOD driving force. This is advantageous because droplets 4 that are not held may otherwise wander under the influence of other, weaker forces. The attenuation of the effective reference voltage for EWOD $V_T$ during the heating period will occur to a greater extent across the reference electrode 28 as the location approaches the connection to $V_{T2}$. The external resistor 50 may therefore optionally be incorporated either on or off the top substrate 36 in order to reduce the proportional resistance and voltage drop, so that the EWOD reference voltage signal for droplet actuation is maintained at an effective level during heating.

This embodiment has some particular advantages including the following:

The reference electrode 28 acting as a heater is in close proximity to the droplet 4 on the electrode array 42, which allows for more efficient and potentially finer control of its temperature, and for more rapid changes in temperature, particularly as compared to a conventional external heater.

The use of a single conductive layer for both EWOD and heating purposes preserves the simplicity of the design and manufacture of EWOD devices. In addition, the structure of the reference electrode 28 as a continuous layer of relatively low resistance means that the voltage drop between points within the area contacted by a droplet 4 is small. In other arrangements such as a meandering electrode pattern, a voltage drop may be observed between nearby points on the same electrode such that if a droplet 4 is in contact with both points, current can flow through the droplet 4 and produce electrolysis, resulting in damage to the device and in chemical changes in the droplet that may interfere with its intended behaviour in subsequent reactions. For such systems, a further dielectric layer covering the electrode is therefore required, which in turn requires the voltage for EWOD actuation to be increased to achieve the same manipulations, which can pose a problem in situations where the available voltages are limited such as in TFT electronics. By comparison, in the present invention, the top substrate 36 may be covered with a hydrophobic coating layer made from a material such as Cytop, and current flow and electrolysis within the droplet 4 are not observed.

The capability of the top substrate to perform a heating function simultaneously with EWOD actuation means that one or more droplets can be manipulated to perform functions such as holding them place, or actively mixing or moving them on the electrode array 42, without interruption to the heating, as is required by some other conventional systems incorporating multifunction electrodes.

It will be apparent to one skilled in the art that a number of variants of the EWOD and heating circuit of FIG. 6 may also be realized, without substantially changing the functionality or principles of operation of the circuit. For example, an AC supply voltage is shown driving $V_{T1}$ in the first embodiment described by FIG. 6, since this is a particularly advantageous mode for effective EWOD actuation in an AM-EWOD device where the TFT electronics limit the maximum voltages that can be used. It should also be noted that EWOD actuation may be achieved with other arrangements, such as a second DC voltage supply 86 connected to this point, and that the heating mode will be facilitated so long as there is a difference between the voltages $V_{T1}$ and $V_{T2}$. It will also be apparent that the supply voltage driving $V_{T1}$ could be driven by a waveform that is of different frequencies at different times. Furthermore, although an AC voltage supply with a square wave profile and a 50% duty cycle is shown in FIG. 7, it will be apparent that $V_{T1}$ can be driven by waveforms with a duty cycle that is not necessarily 50% or that have a different profile such as a sawtooth or sigmoid wave.

In addition, while the reference electrode 28 is shown as a single region of conductive material with one pair of connections A and B at voltages $V_{T1}$ and $V_{T2}$, in alternative embodiments the reference electrode 28 could be divided into two or more regions forming two or more reference electrodes to be driven separately in order to allow regional control of the temperature, by which different temperatures are attained in different regions. A disadvantage of such embodiments is that movement or other manipulation of droplets 4 must be carefully choreographed to avoid the situation in which any droplet 4 spans the gap between two reference electrodes 28 that are locally at different voltages, since this creates the opportunity for a current to flow and electrolysis to occur. This situation can arise in heating mode where there are variations either in the resistance of the electrodes or between the voltages used to drive the electrodes.

Figure 8:
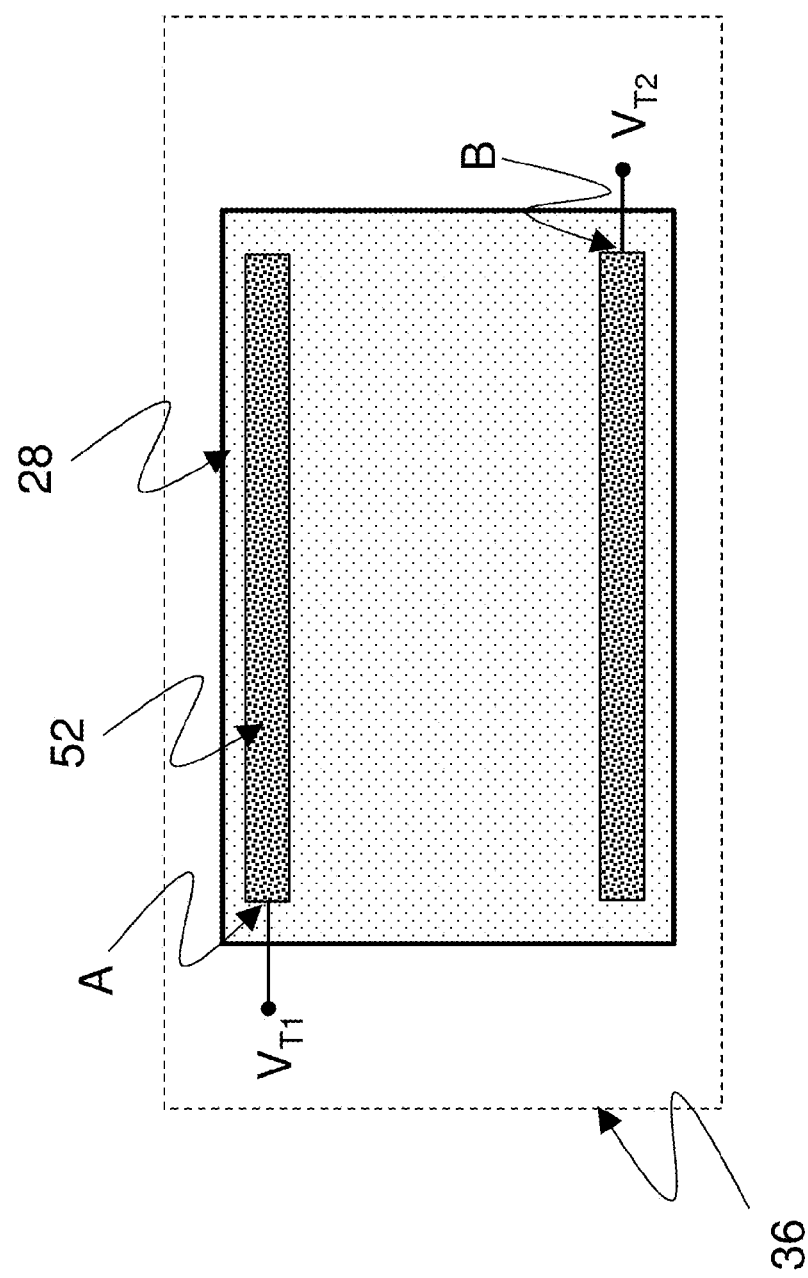
FIG. 8 is a schematic diagram depicting an overhead view of the top substrate of the exemplary AM-EWOD device of FIG. 4, and a method of making connections so as to allow EWOD actuation and heating according to an exemplary second embodiment.

FIG. 8 is a schematic diagram depicting the top substrate 36 of the AM-EWOD device 41 of FIG. 3 in an overhead view according to a second exemplary embodiment. In the second embodiment, the reference electrode 28 of the first embodiment shown in FIG. 5 is modified to incorporate a plurality of first regions of low resistance (high conductance) 52. This may be achieved by patterning or otherwise adjusting the thickness of the conductive material, such as ITO, from which electrode is formed such that the second regions or other parts of the reference electrode 28 are of higher resistance, or alternatively by composition of the electrode from two or more different materials, in which case the low resistance regions 52 may be made of a material with a higher conductance.

Advantages of this second embodiment include
i) When connecting the reference electrode 28 to the external circuitry, a low resistance contact can be more easily formed with the low resistance regions 52.
ii) The low resistance regions running in parallel along the length of the reference electrode act as an extension of the driving circuit such that the current flow across the higher resistance region between them should be more homogenous compared to the arrangement in FIG. 5.

Figure 9:
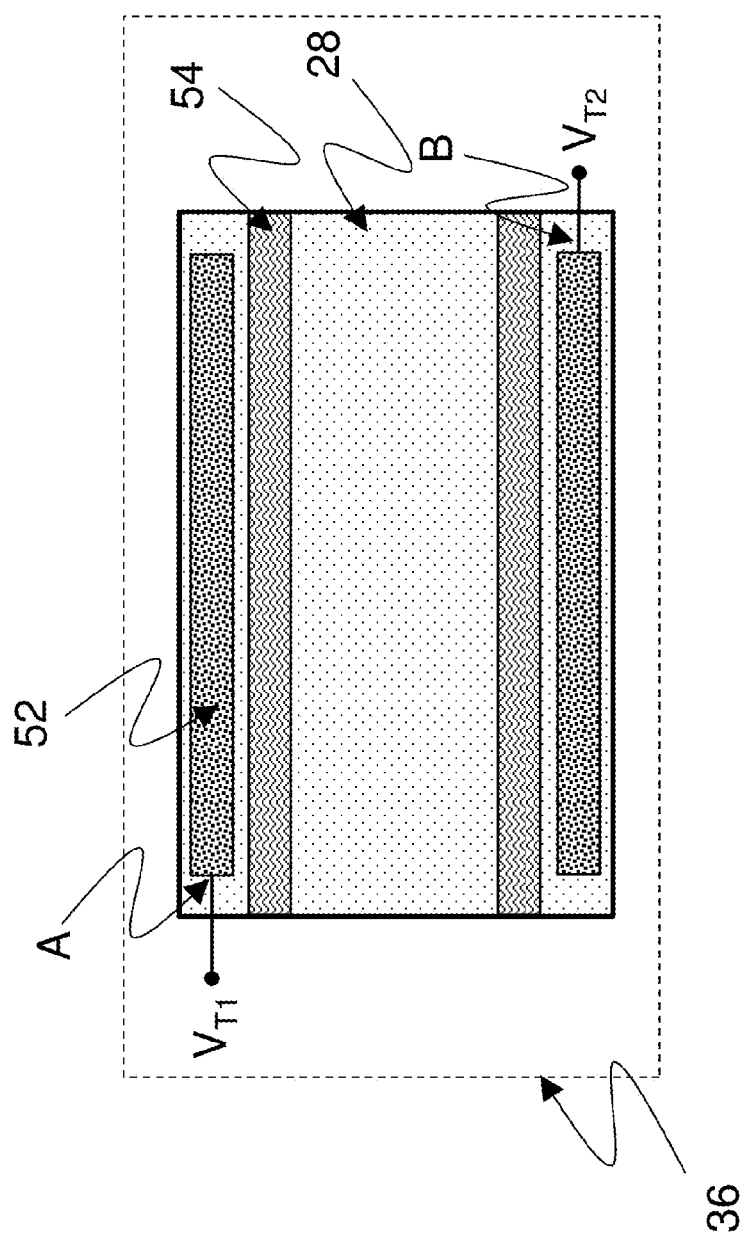
FIG. 9 is a schematic diagram depicting an overhead view of the top substrate of the exemplary AM-EWOD device of FIG. 4, and a method of making connections so as to allow EWOD actuation and heating according to an exemplary third embodiment.

FIG. 9 is a schematic diagram depicting the top substrate 36 of the AM-EWOD device 41 of FIG. 3 in an overhead view according to a third exemplary embodiment. In the third embodiment, the reference electrode 28 of the second embodiment shown in FIG. 8 is modified to incorporate a plurality of third regions of high resistance 54 having a higher resistance (lower conductance) as compared to the first or second regions. This may be achieved by patterning or otherwise adjusting the thickness of the conductive material, such as ITO, from which electrode is formed, or alternatively by composition of the electrode from two or more different materials. The advantages of this embodiment include the capability to produce an uneven distribution of heating across the surface of the reference electrode, with the high resistance regions 54 dissipating proportionately more heat. In a cartridge 44 the surrounding material of the AM-EWOD device 41 may be at a lower temperature than the device itself during heating, and the result will be a propensity for the edges of the AM-EWOD device 41 to lose heat by conduction and for the temperature to fall off from the centre of the electrode array 42. In the arrangement described in this embodiment, the parts of the AM-EWOD device 41 close to the edges of the reference electrode 28 will be heated most, which may serve to counteract the conductive cooling effect and thus produce a more even temperature across the electrode array 42. It will be clear to a person skilled in the art that other configurations using non-uniform resistance in the reference electrode 28 are possible to shape the heating achieved in different ways, such as to create one or more heating and temperature gradients across the electrode array 42.

Figure 10:
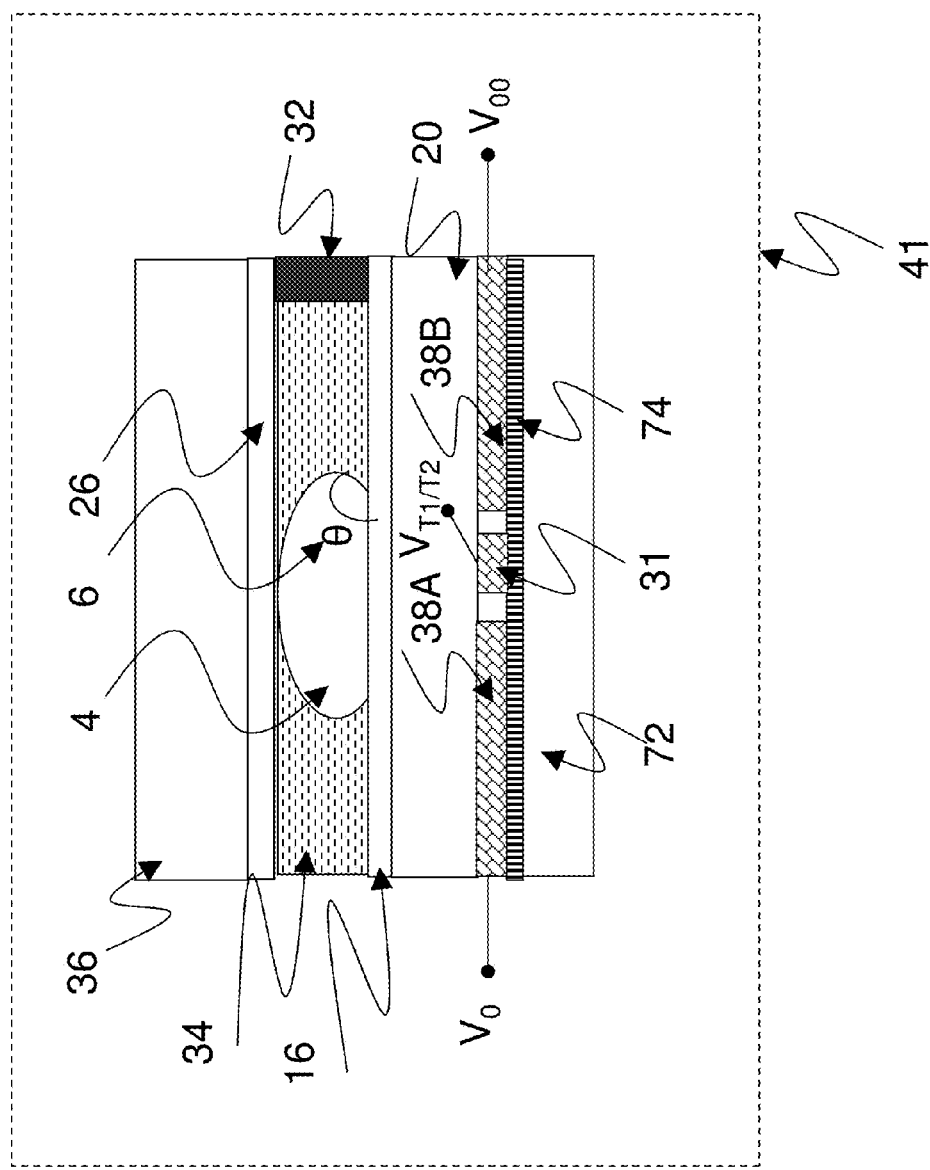
FIG. 10 shows a cross section through some of the array elements of an AM-EWOD device according to an exemplary fourth embodiment with an alternative design incorporating an in-plane reference electrode on the bottom substrate.

FIG. 10 is a schematic diagram depicting an AM-EWOD device 41, such as the device of FIG. 3, in cross-section and including a pair of the array elements 38A and 38B in an alternative exemplary fourth embodiment of the invention. FIG. 10 is similar to FIG. 4, but omits the top reference electrode 28 in the top substrate 36 and instead incorporates a layer of conductive material patterned in order to form an in-plane reference electrode 31 running between the array elements 38A and 38B on the bottom substrate 72.

Figure 11:
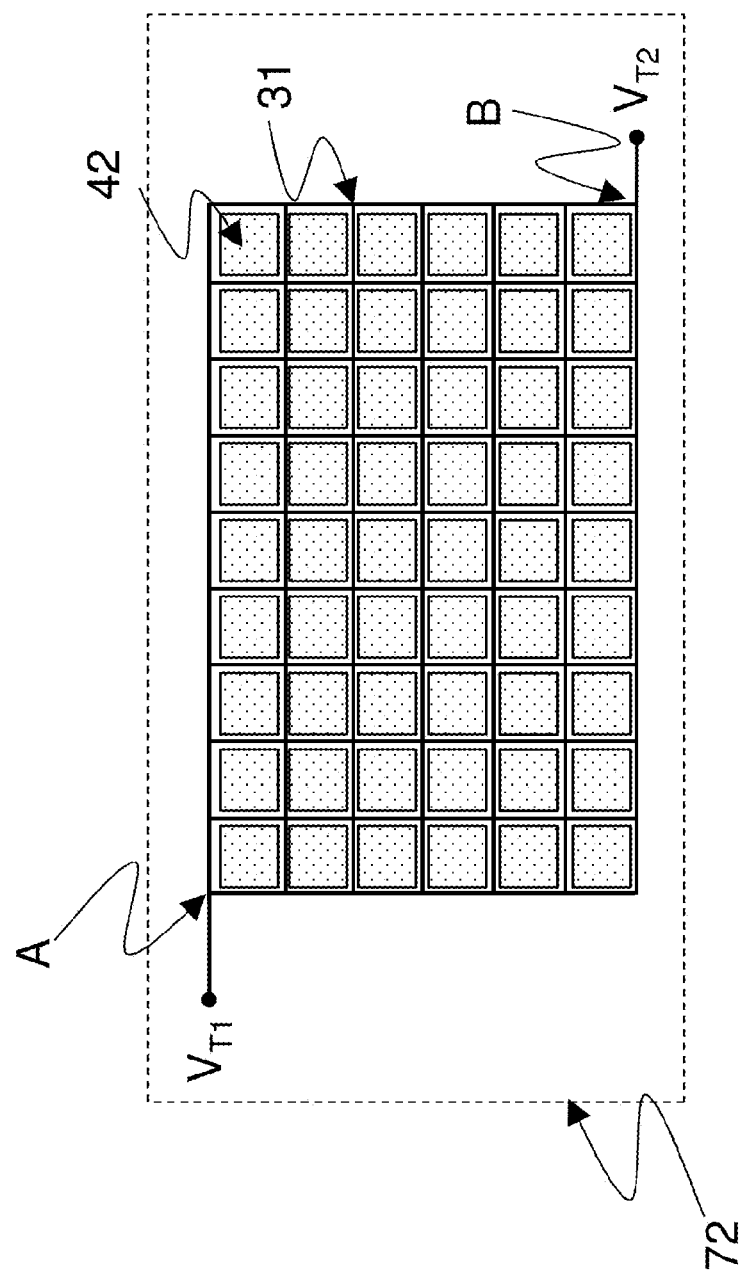
FIG. 11 is a schematic diagram depicting an overhead view of the bottom substrate of an AM-EWOD device with an alternative design incorporating a reference electrode on the bottom substrate, and a method of making connections so as to allow EWOD actuation and heating according to an exemplary fourth embodiment.

FIG. 11 shows an overhead view of bottom substrate 72 of the AM-EWOD device 41 shown in FIG. 10. The in-plane reference electrode 31 is depicted in a grid pattern in the spaces between the array elements 38 to form an in-plane reference electrode 31 on the bottom substrate 72.

The in-plane reference electrode 31 may be driven by $V_{T1}$ and $V_{T2}$ at connections A and B using a similar circuit to that described previously and depicted in FIG. 6, replacing the reference electrode 28 in the top substrate 36 with the in-plane reference electrode 31. In the fourth embodiment depicted in FIG. 10, the in-plane reference electrode 31 is made by patterning the same conductive layer as is used for the array elements 38, which has the disadvantage of reducing the efficacy of a given electrowetting voltage $V_{EWOD}$ for producing EWOD actuation since there are two passes through the dielectric layer 20. However, as is noted previously, alternative structures are possible which will not be as affected by this, including an in-plane reference electrode 31 formed in a separate layer or specific etching or deposition of the dielectric layer 20 so as to expose the in-plane reference electrode 31 and allow it to directly contact the hydrophobic layer 16.

Advantages of this fourth embodiment include simplifying the design of the electrical connections in a cartridge 44, and the ability to incorporate alternative additional functionality into the top substrate 36.

Figure 12:
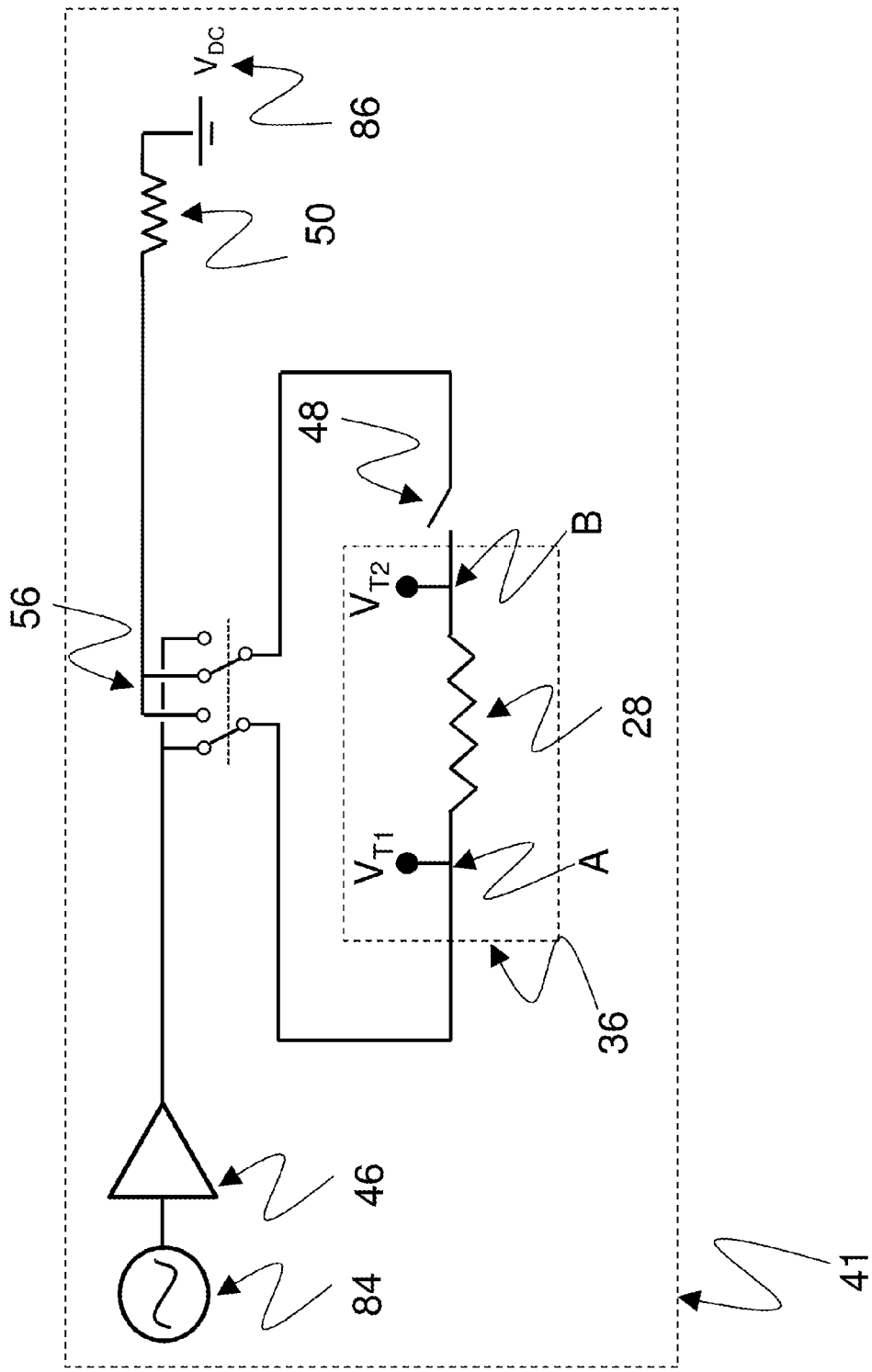
FIG. 12 shows a circuit representation of the reference electrode and its electrical connections in FIG. 5 according to an exemplary fifth embodiment, allowing it to be driven to achieve EWOD actuation and joule heating.

FIG. 12 shows a circuit representation of the reference electrode 28 of FIG. 5 and an exemplary mode of forming the electrical connections and voltages that are used for driving it for EWOD actuation and heating, according to an exemplary fifth embodiment. In this case the AC driving voltage supply 84 and DC sink voltage 86 of the first embodiment are connected to the reference electrode 28 via a double pole double throw four way switch 56, allowing the sources for the voltages driving $V_{T1}$ and $V_{T2}$ to be switched. The advantages of this embodiment include the ability to select which part of the electrode array 42 experiences an attenuated reference voltage $V_T$ for EWOD actuation.

Figure 13:
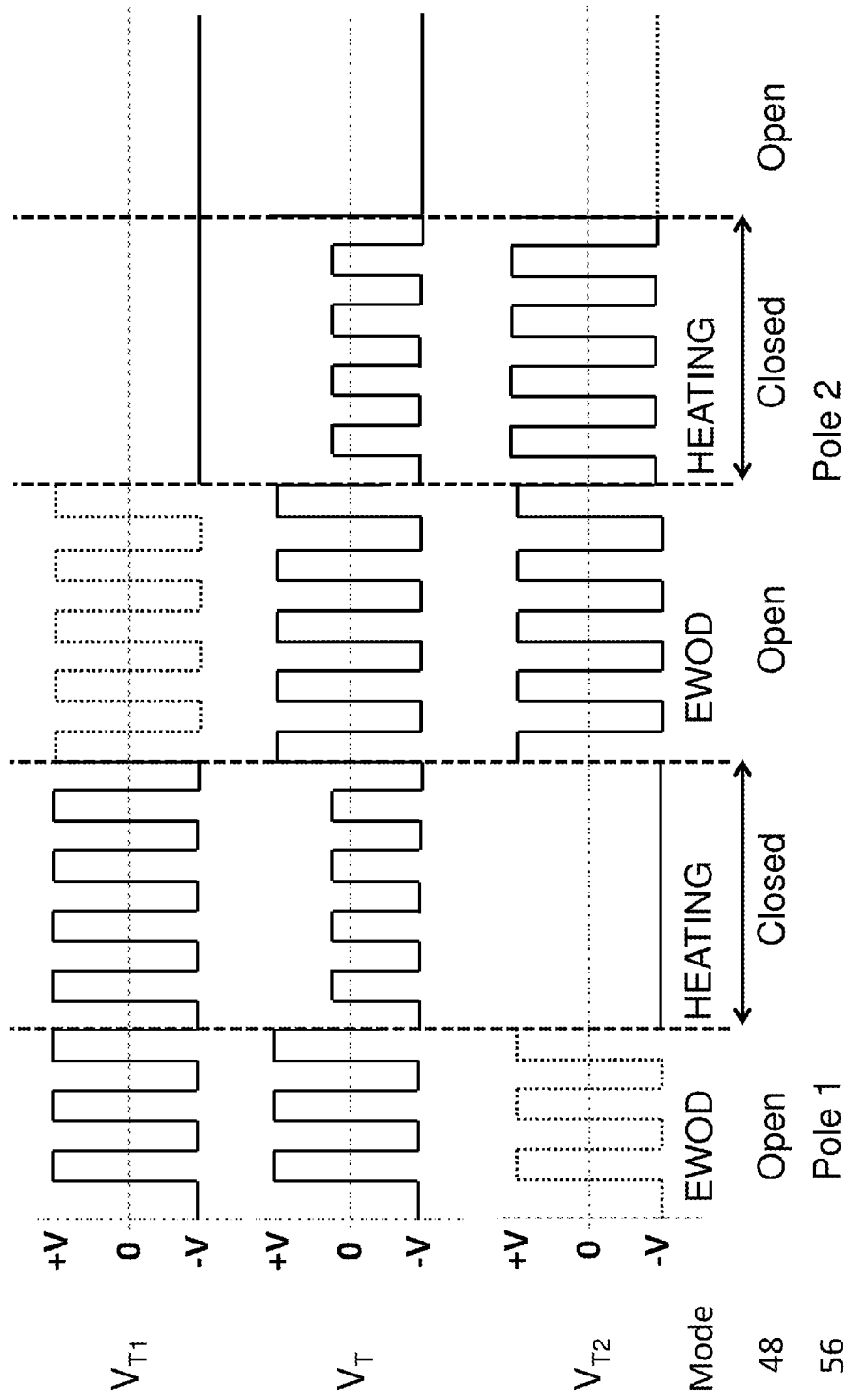
FIG. 13 is a graphical representation of the voltages $V_{T1}$ and $V_{T2}$ that are connected to the reference electrode of FIG. 5 and the voltage observed on the electrode itself.

FIG. 13 is a graphical representation similar to FIG. 7, displaying examples of the voltages $V_{T1}$ and $V_{T2}$ observed at connections A and B and the effective reference voltage for EWOD actuation in the reference electrode 28, $V_T$, when driven according to the fifth embodiment using the circuit depicted in FIG. 12. As for the first embodiment shown in FIG. 7, whether the system is in EWOD mode or heating mode is controlled primarily by the state of switch 48. In this embodiment, however, the state of the double pole double throw switch 56 controls which of $V_{T1}$ and $V_{T2}$ is driven by the AC signal and the DC signal. Thus, EWOD mode is selected when the switch 48 is open, in which case all of $V_{T1}$, $V_{T2}$ and $V_T$ will be driven by whichever voltage supply is connected to $V_{T1}$ by the double pole double throw switch 56. As in FIG. 7, the waveform at $V_{T2}$ is shown as a dotted line during EWOD mode to emphasize the fact that it is being passively driven by the same voltage supply $V_{T2}$. Heating mode is selected when the switch 48 is closed and as for FIG. 7, the waveform of the voltage observed at $V_T$ at a respective location along the reference electrode 28 is a combination of the voltages $V_{T1}$ and $V_{T2}$ connected at connections A and B, resulting in an attenuated version of the signal from the AC voltage supply 84. For the purposes of illustration, the effect on $V_T$ of opening switch 48 with the double pole double throw switch 56 in position 2 is shown in FIG. 13, connecting the reference electrode solely to the DC voltage supply 86, though this arrangement is unlikely to be used for AM-EWOD driving in practice.

Figure 14:
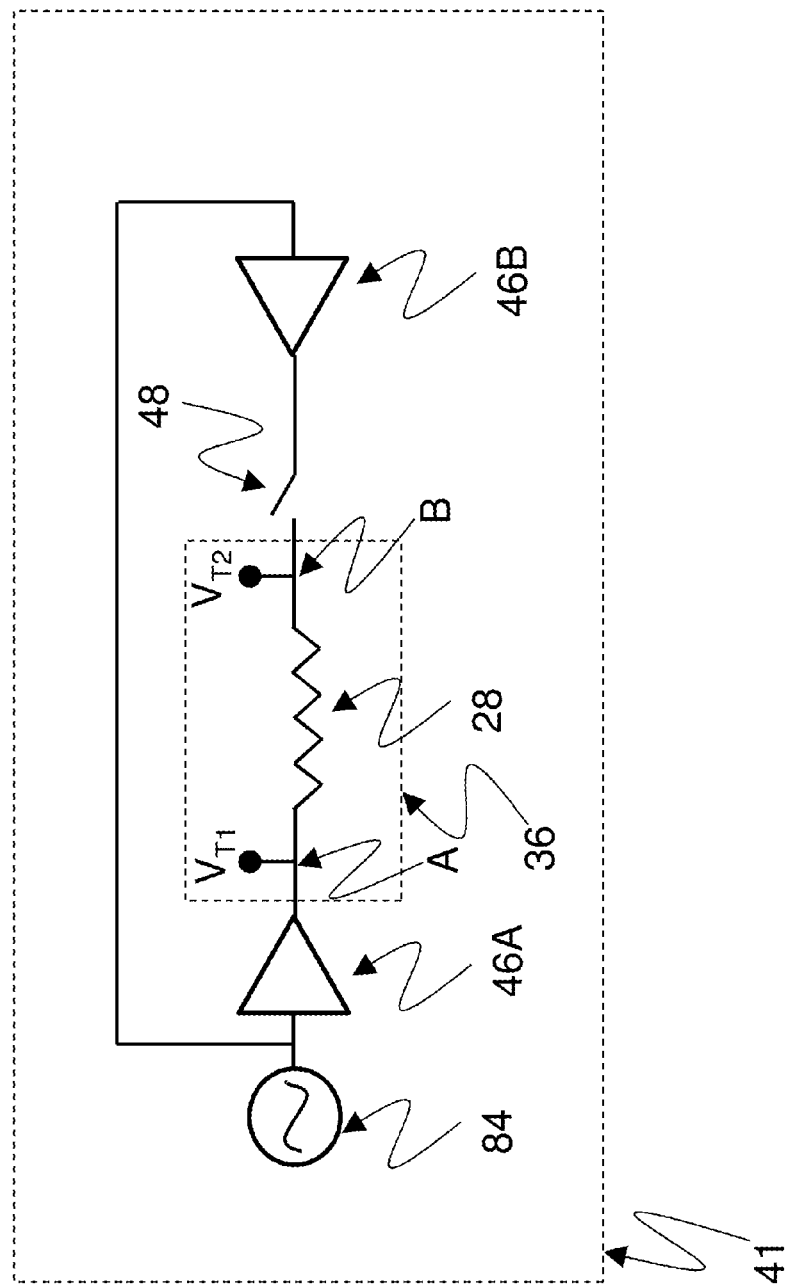
FIG. 14 shows a circuit representation of the reference electrode and its electrical connections in FIG. 5 according to an exemplary sixth embodiment, allowing it to be driven to achieve EWOD actuation and joule heating.

FIG. 14 shows a circuit representation of the of the reference electrode 28 of FIG. 5 and an alternative mode of forming the electrical connections and voltages that are used to drive it for EWOD actuation and heating, according to an exemplary sixth embodiment. Many elements of this circuit are the same as that of the first embodiment, portrayed in FIG. 6, with the reference electrode 28 connected at connection A to an AC supply 84 via a first output amplifier 46A. However, in the circuit of the sixth embodiment, the DC voltage supply 86 of the first embodiment is replaced with a separate connection from node $V_{T2}$ to the AC voltage supply 84, via a second output amplifier 46B, which has a different gain as compared to the first output amplifier 46A. For example, the output amplifiers 46A and 46B may have gains of 1 and 0.7 respectively. This enables a potential difference to be achieved across the reference electrode 28 to produce heating, while maintaining a reference voltage for EWOD actuation that will be no less than the signal multiplied by the gain of the second output amplifier 46B. The resistor 50 is no longer required and can be omitted. If the gain of the second output amplifier 46B is variable then temperature control can be achieved not only by the control of the duty cycle of the heating mode relative to the EWOD mode by switch 48, but also by varying the gain and thereby the voltage $V_{T2}$ observed at connection B and ultimately the heating produced. Optionally, if the gain of the second output amplifier 46B were variable, then the switch 48 could also be omitted, since EWOD-only mode could be achieved by matching the gains and the voltages $V_{T1}$ and $V_{T2}$ instead of opening the switch 48.

FIG. 15 is a graphical representation of the voltages $V_{T1}$ and $V_{T2}$ observed at connections A and B and of the effective reference voltage for EWOD actuation in the reference electrode 28, $V_T$, over a short period of time, according to the fifth embodiment of the device depicted in FIG. 14. As in FIG. 7, two distinct operating modes are shown, with EWOD mode facilitated by opening switch 48 and heating mode facilitated by closing the same switch 48. Similarly to the EWOD mode shown in FIG. 7, in the sixth embodiment during EWOD mode the reference electrode is connected only via connection A to the AC voltage signal issuing from the output amplifier 46A. $V_T$ and $V_{T2}$ are therefore driven to the same voltage as $V_{T1}$, and once more the waveform at $V_{T2}$ is shown with a dotted line to emphasize that it is not being driven by a second connection. When switch 48 is closed and the heating mode is activated, connection B is connected to the second output amplifier 46B and is shown being actively driven as $V_{T2}$ but with a voltage signal of reduced amplitude resulting from the lower gain of the output amplifier 46B. During this period $V_T$ therefore assumes an intermediate voltage between the two versions of the AC voltage supply 84.

Advantages of this sixth embodiment include:
i) The potential for heating with less interruption to EWOD actuation, since there is the option to provide more continuous heating with slight reduction in EWOD voltage, rather than brief periods of more significant reduction.
ii) Avoiding dissipating heat in resistor 50 found in other circuit embodiments.

An aspect of the invention, therefore, is an electrowetting on dielectric (EWOD) device. In exemplary embodiments, the EWOD device includes a reference electrode, a plurality of array elements, each array element including an array element electrode, and control electronics configured to control a supply of time varying voltages to the array element electrodes and the reference electrode, thereby generating an actuation voltage as a potential difference between voltages at the array element electrodes and the reference electrode. The reference electrode includes a first electrical connection and a second electrical connection, and the control electronics further is configured to supply an electrical current flow between the first electrical connection and the second electrical connection to generate resistance heat for controlling temperature of the EWOD device.

In an exemplary embodiment of the EWOD device, the control electronics includes a first voltage supply for supplying a voltage to the first electrical connection, and a second voltage supply for supplying a voltage to the second electrical connection.

In an exemplary embodiment of the EWOD device, the control electronics further includes a switch located between the second voltage supply and the second electrical connection. The switch is switchable between an open position and a closed position, the open position corresponding to an EWOD actuation mode in which there is no current flow between the first electrical connection and the second electrical connection, and the closed position corresponding to a heating mode in which current flows between the first electrical connection and the second electrical connection to generate the resistance heat for controlling temperature the EWOD device.

In an exemplary embodiment of the EWOD device, the control electronics further includes a first amplifier located between the first voltage supply and the first electrical connection for maintaining the voltage supply to the first electrical connection.

In an exemplary embodiment of the EWOD device, the first voltage supply is an alternating current (AC) voltage supply, and the second voltage supply is a direct current (DC) voltage supply.

In an exemplary embodiment of the EWOD device, the control electronics further includes a resistor between the second voltage supply and the second electrical connection, the resistor operating to reduce a proportional resistance of, and voltage drop across, the reference electrode.

In an exemplary embodiment of the EWOD device, the control electronics further includes a double pole switch for switching source voltages to the first electrical connection and the second electrical connection.

In an exemplary embodiment of the EWOD device, the first voltage supply is an alternating current (AC) voltage supply, and the second voltage supply is supplied by inputting the first voltage supply to a second amplifier electrically connected with the second electrical connection, the second amplifier having a different gain from the first amplifier.

In an exemplary embodiment of the EWOD device, the reference electrode has a plurality of first regions of low resistance having a higher conductance relative to other second regions of the reference electrode.

In an exemplary embodiment of the EWOD device, the reference electrode has a plurality of third regions of high resistance having a lower conductance relative to the first and second regions of the reference electrode.

In an exemplary embodiment of the EWOD device, the first and/or third regions run in parallel along a length of the reference electrode.

In an exemplary embodiment of the EWOD device, the reference electrode comprises a conductive material formed in plane with the array element electrodes.

In an exemplary embodiment of the EWOD device, the EWOD device further includes thin film electronics that includes at least a portion of the control electronics, a substrate upon which the thin film electronics is disposed, and a non-transitory computer readable medium storing a computer program that is executed to control the control electronics.

In an exemplary embodiment of the EWOD device, the EWOD device is an active matrix electrowetting on dielectric (AM-EWOD) device Another aspect of the invention is a method of controlling an electrowetting on dielectric (EWOD) device, the EWOD device comprising a reference electrode and a plurality of array elements, each array element including an array element electrode. The control method includes the steps of: operating in a first mode for optimized EWOD actuation by supplying time varying voltages to the array element electrodes and the reference electrode, thereby generating an actuation voltage as a potential difference between voltages at the array element electrodes and the reference electrode; and operating in a second mode for temperature control further by supplying an electrical current flow across the reference electrode to generate resistance heat for controlling temperature of the EWOD device.

In an exemplary embodiment of the control method, the control method further includes sensing a temperature of the EWOD device, and switching between operating in the first mode or the second mode based on the sensed temperature.

In an exemplary embodiment of the control method, the control method, further includes using a feedback mechanism for controlling temperature of the EWOD device.

In an exemplary embodiment of the control method, in the second mode the actuation voltage is attenuated, the method further comprising maintaining the actuation voltage in the second mode at a level adequate to perform a low-voltage droplet operation.

In an exemplary embodiment of the control method, the low-voltage droplet operation comprises maintaining a position of a droplet in the EWOD device.

In an exemplary embodiment of the control method, the reference electrode is divided into at least a first region and a second region, the control method further comprising operating in the second mode to attain different temperatures in the first and second regions.

Although the invention has been shown and described with respect to a certain embodiment or embodiments, equivalent alterations and modifications may occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein exemplary embodiment or embodiments of the invention. In addition, while a particular feature of the invention may have been described above with respect to only one or more of several embodiments, such feature may be combined with one or more other features of the other embodiments, as may be desired and advantageous for any given or particular application.

INDUSTRIAL APPLICABILITY

The described embodiments could be used to provide a microfluidic device utilising the EWOD principle with a means of controlling the temperature of fluids on the chip. The EWOD device could form a part of a lab-on-a-chip system. Such devices could be used in manipulating, reacting and sensing chemical, biochemical or physiological materials. Applications include healthcare diagnostic testing, material testing, chemical or biochemical material synthesis, proteomics, tools for research in life sciences and forensic science.

The invention claimed is:

1. An electrowetting on dielectric (EWOD) device comprising:
   a first substrate on which there is deposited a reference electrode;
   a plurality of array elements including a second substrate different from the first substrate on which there is deposited a plurality of array element electrodes, the first and second substrates defining a gap for receiving a droplet, and each array element including an array element electrode from among the plurality of array element electrodes; and
   control electronics configured to control a supply of time varying voltages to the array element electrodes and the reference electrode, thereby generating an actuation voltage as a potential difference between voltages at the array element electrodes and the reference electrode;
   wherein:
   the reference electrode includes a first electrical connection and a second electrical connection, and the control electronics further is configured to supply an electrical current flow between the first electrical connection and the second electrical connection to generate resistance heat for controlling temperature of the EWOD device;
   the control electronics includes a first voltage supply for supplying a voltage to the first electrical connection, and a second voltage supply for supplying a voltage to the second electrical connection;
   the control electronics further includes a switch located between the second voltage supply and the second electrical connection; and
   wherein the switch is switchable between an open position and a closed position, the open position corresponding to an EWOD actuation mode in which there is no current flow between the first electrical connection and the second electrical connection, and the closed position corresponding to a heating mode in which current flows between the first electrical connection and the second electrical connection to generate the resistance heat for controlling temperature the EWOD device.

2. An electrowetting on dielectric (EWOD) device comprising:
   a reference electrode;
   a plurality of array elements including a plurality of array element electrodes, each array element including an array element electrode from among the plurality of array element electrodes; and
   control electronics configured to control a supply of time varying voltages to the array element electrodes and the reference electrode, thereby generating an actuation voltage as a potential difference between voltages at the array element electrodes and the reference electrode;
   wherein:
   the reference electrode includes a first electrical connection and a second electrical connection, and the control electronics further is configured to supply an electrical current flow between the first electrical connection and the second electrical connection to generate resistance heat for controlling temperature of the EWOD device;
   the control electronics includes a first voltage supply for supplying a voltage to the first electrical connection, and a second voltage supply for supplying a voltage to the second electrical connection;
   the control electronics further includes a switch located between the second voltage supply and the second electrical connection; and
   the switch is switchable between an open position and a closed position, the open position corresponding to an EWOD actuation mode in which there is no current flow between the first electrical connection and the second electrical connection, and the closed position corresponding to a heating mode in which current flows between the first electrical connection and the second electrical connection to generate the resistance heat for controlling temperature the EWOD device.

3. The EWOD device of claim 2, wherein the control electronics further includes a first amplifier located between the first voltage supply and the first electrical connection for maintaining the voltage supply to the first electrical connection.

4. The EWOD device of claim 2, wherein the first voltage supply is an alternating current (AC) voltage supply, and the second voltage supply is a direct current (DC) voltage supply.

5. The EWOD device of claim 2, wherein the control electronics further includes a resistor between the second voltage supply and the second electrical connection, the resistor operating to reduce a proportional resistance of, and voltage drop across, the reference electrode.

6. The EWOD device of claim 2, wherein the control electronics further includes a double pole switch for switching source voltages to the first electrical connection and the second electrical connection.

7. The EWOD device of claim 3, wherein the first voltage supply is an alternating current (AC) voltage supply, and the second voltage supply is supplied by second electrical connection, the second amplifier having a different gain from the first amplifier.

8. The EWOD device of claim 2, wherein the reference electrode has a plurality of first regions of low resistance having a higher conductance relative to other second regions of the reference electrode.

9. The EWOD device of claim 2, further comprising:
   thin film electronics that includes at least a portion of the control electronics;
   the thin film electronics being disposed on the second substrate; and
   a non-transitory computer readable medium storing a computer program that is executed to control the control electronics.

10. The EWOD device of claim 8, wherein the reference electrode has a plurality of third regions of high resistance having a lower conductance relative to the first and second regions of the reference electrode.

11. The EWOD device of claim 8, wherein the first and/or third regions run in parallel along a length of the reference electrode.

12. The EWOD device of claim 2, wherein the EWOD device is an active matrix electrowetting on dielectric (AM-EWOD) device.

13. An electrowetting on dielectric (EWOD) device comprising:
a reference electrode;
a plurality of array elements including a plurality of array element electrodes, each array element including an array element electrode from among the plurality of array element electrodes; and
control electronics configured to control a supply of time varying voltages to the array element electrodes and the reference electrode, thereby generating an actuation voltage as a potential difference between voltages at the array element electrodes and the reference electrode;
wherein:
the reference electrode includes a first electrical connection and a second electrical connection, and the control electronics further is configured to supply an electrical current flow between the first electrical connection and the second electrical connection to generate resistance heat for controlling temperature of the EWOD device;
the control electronics includes a first voltage supply for supplying a voltage to the first electrical connection, and a second voltage supply for supplying a voltage to the second electrical connection; and
wherein the control electronics further includes a resistor between the second voltage supply and the second electrical connection, the resistor operating to reduce a proportional resistance of, and voltage drop across, the reference electrode.

14. The EWOD device of claim 13, wherein the first voltage supply is an alternating current (AC) voltage supply, and the second voltage supply is a direct current (DC) voltage supply.

15. The EWOD device of claim 13, wherein the control electronics further includes a double pole switch for switching source voltages to the first electrical connection and the second electrical connection.

* * * * *